United States Patent [19]
Larkin et al.

[11] Patent Number: 4,847,417
[45] Date of Patent: Jul. 11, 1989

[54] BIS(DIAMINOPOLYALKOXY)-N-ALKYLAMINES BY AMINATION OF HYDROXYL-CONTAINING TERTIARY AMINES

[75] Inventors: John M. Larkin; George P. Speranza, both of Austin, Tex.

[73] Assignee: Texaco Inc., White Plains, N.Y.

[21] Appl. No.: 262,755

[22] Filed: Oct. 26, 1988

Related U.S. Application Data

[62] Division of Ser. No. 80,929, Aug. 3, 1987.

[51] Int. Cl.$^4$ ............... C07C 85/02; C07C 85/06; C07C 93/04
[52] U.S. Cl. ................... 564/475; 564/474; 564/480; 564/505
[58] Field of Search ............ 564/475, 480, 505, 474

[56] References Cited

U.S. PATENT DOCUMENTS 3,654,370  4/1972  Yeakey ............................ 260/584 B
3,706,676  12/1972  Franke et al. ...................... 252/544

Primary Examiner—Glennon H. Hollrah
Assistant Examiner—Peter G. O'Sullivan
Attorney, Agent, or Firm—Jack H. Park; Kenneth R. Priem; Richard A. Morgan

[57] ABSTRACT

A method for converting a bis(polyalkoxy)-N-alkylamine to a bis(diaminopolyalkoxy)-N-alkylamine has been discovered. The method comprises alkoxylating an alkylamine to a bis(polyalkoxy)-N-alkylamine. The alkylamine is selected to sterically hinder the resulting tertiary amine. The alkoxylate is then catalytically aminated according to well known procedures with a high yield of the diamine resulting.

Compounds prepared by this method are of the formula:

$$R-N-(PO_x-NH_2)_2$$

wherein:
PO is propylene oxide,
x ranges from 2 to 40, and
R is a sterically hindering alkyl such as isopropyl or tertiary butyl.

The compounds are useful for curing epoxy thermoset resins. They are uniquely suited to reactions with polyisocyanates to prepare plastic parts, such as automobile body panels, by reaction injection molding.

5 Claims, No Drawings

BIS(DIAMINOPOLYALKOXY)-N-ALKYLAMINES BY AMINATION OF HYDROXYL-CONTAINING TERTIARY AMINES

This is a division of application Ser. No. 080,929, filed Aug. 3, 1987.

CROSS REFERENCE TO RELATED APPLICATION

This invention is related to U.S. Patent Application titled Nitrile(Tris) Polyoxyalkyleneamines in a Reaction Injection Molding Process, by John M. Larkin and Michael Cuscurida, Ser. No. 080,930 filed on Aug. 3, 1987.

FIELD OF THE INVENTION

The invention is a method for aminating hydroxyl-containing tertiary amines and the compounds produced thereby. More particularly, the invention is a method for aminating a bis(polyalkoxy)-N-alkylamine to a novel bis(diaminopolyalkoxy)-N-alkylamine.

DESCRIPTION OF OTHER RELEVANT METHODS IN THE FIELD

The amination of long alkoxylated alkyl chains terminated by hydroxyl groups is well known in the art.

U.S. Pat. No. 3,654,370 to E. L. Yeakey teaches the amination of polyoxyalkylene polyols to form the corresponding amines by means of ammonia and hydrogen over a catalyst prepared by the reduction of a mixture of the oxides of nickel, copper and chromium. The amination is carried out at a temperature of 150° to 275° C. and 500 to 5000 psig.

U.S. Pat. No. 4,409,399 to H. E. Swift et al. teaches a catalyst for aminating aliphatic alcohols and aldehydes. The unsupported catalyst comprises (1) copper oxide or copper hydroxide and (2) nickel oxide or nickel hydroxide, and optionally (3) an oxide or hydroxide of a Group IIA, e.g. magnesium, barium. The reaction is carried out at a temperature of 150° to 250° C. and 1 to 100 atm with continuous water removal.

U.S. Pat. No. 3,390,184 to P. H. Moss et al. teaches a process for converting a secondary alcohol to a high molecular weight primary amine by means of a hydrogenation-dehydrogenation catalyst comprising at least one member selected from the group consisting of the metals and oxides of nickel and cobalt, together with copper and a metal oxide selected from the group consisting of chromium oxide, molybdenum oxide, manganese oxide and thorium oxide. The reaction is carried out at a temperature of 225° to 260° C. and pressure of 2000 to 4000 psig, with ammonia as the aminating agent.

U.S. Pat. No. 3,373,204 to R. A. Hales et al. teaches a catalytic process for producing secondary amines from derivatives of phenols, alcohols and amines containing 5 to 40 moles of ethylene oxide and propylene oxide. The catalyst is Raney nickel and ammonia or primary alkylamines are the aminating agent. The reaction is carried out at 200° to 275° C. with the evolution of water. Amines include lauryl amine, headecyl amine, octadecyl amine, rosin amine and fatty acid amines.

U.S. Pat. No. 3,347,926 to J. D. Zech teaches a catalytic process for aminating primary and secondary aliphatic alcohols. The catalyst comprises a chromium promoted Raney nickel. The reaction is carried out at 150° C. to 275° C. with ammonia, primary amines or secondary amines of 1 to 6 carbon atoms.

U.S. Pat. No. 2,923,696 to K. E. Harwell et al. teaches resinous compositions formed by the reaction of an epoxy resin with a high boiling amine product. The patent further teaches hydrogenation catalysts employing copper, nickel, copper and oxides thereof.

U.S. Pat. No. 4,130,590 to Hobbs et al. teaches the production of long chain unsaturated amines such as N-(alkadienyl)amines and saturated or hydrated derivatives thereof.

SUMMARY OF THE INVENTION

The invention is a method for producing a bis(diaminopolyalkoxy)-N-alkylamine. The method comprises alkoxylating an alkylamine to a bis(polyalkoxy)-N-alkylamine. This product is catalytically aminated with ammonia to a bis(diaminopolyalkoxy)-N-alkylamine.

The improvement comprises a sterically hindering alkyl in the alkylamine. The hindering alkyl prevents attack of the tertiary amine, thereby facilitating amination of the hydroxyl group at the end of the alkylene oxide chain.

The invention also relates to compounds synthesized by the method. These compounds are useful for producing thermoset epoxy resins, polyureas and polyamines.

DESCRIPTION OF THE PREFERRED EMBODIMENTS

We have discovered that bis(polyalkoxy)-N-alkylamines can be directly converted to the corresponding diamines by reaction with ammonia in the liquid phase at a temperature of 180° to 250° C., preferably 210° to 240° C. and pressure of 500 to 3000 psig, preferably 1000 to 2500 psig over amination catalyst, often referred to as hydrogenation/dehydrogenation catalyst.

Such a hydrogenation/dehydrogenation catalyst is the nickel, copper, chromium catalyst of U.S. Pat. No. 3,654,370 to Yeakey incorporated herein by reference. Raney nickel and promoted Raney nickel, e.g. molybdenum promoted Raney nickel, are also satisfactory.

The choice of an alkylamine starting material has been found to be absolutely critical. The alkyl must be sufficiently branched to sterically hinder the tertiary amine from attack in the catalytic amination. We show in a comparative example that if attack of the tertiary amine is not hindered, the identical process conditions yield an array of degradation products. By way of example, when compounds such:

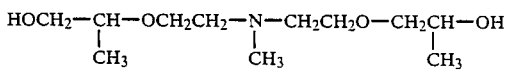

are aminated, migration of the methyl group and cleavage of the chain at the nitrogen atom predominates.

Accordingly, the most preferred starting materials include isopropyl amine; tertiary butyl amine; isobutyl amine; isopentyl amine; 1,1,3,3-tetramethylbutyl amine and 2,4-diamino-2-methylpentane. Other starting materials include branched and highly branched alkyls of 3 to 12 carbon atoms, for example the amines of neopentane, isohexane, neohexane, 2,2,4-trimethylpentane, 2,2-dimethylbutane, 2,3-dimethylbutane.

The alkoxylation is carried out according to methods well known in the art and described in the Examples.

Preferred alkylene oxides are propylene oxide, butylene oxide and mixtures thereof.

The amines of our method are primarily useful as curing agents for epoxy thermoset resins. They may also be used in the preparation of polyureas and polyamides. They are uniquely suitable in reactions with polyisocyanates to prepare urethane elastoner parts, such as automobile body panels, by reaction injection molding. Polyamides can be prepared by allowing the compounds to react with dibasic acids, diesters and diacid chlorides.

This invention is better shown by way of Example.

EXAMPLE 1

Amination of Polypropoxylate of 2,4-Diamino-2-Methylpentane

A one liter stirred autoclave was charged with 14.999 g of anhydrous Raney 3000 (2% Mo-promoted Raney nickel from W. R. Grace and Co.) and 140.2 g of a polypropoxylated 2,4-diamino-2-methylpentane of 2020 molecular weight. The atmosphere in the autoclave was replaced with hydrogen, and 18.2 g of $NH_3$ was charged. The autoclave was pressured to 380 psig with hydrogen at 20.2° C. It was heated to 234° C. during a 46 minute period and held at approximately 236° C. for 20 minutes. Pressure declined from 980 to 930 psig during this time. It was cooled to room temperature, vented, and the contents filtered and stripped (99° C., 20 mm Hg, rotary evaporator).

The clear colorless liquid with a mild ammoniacal odor analyzed as follows: total acetylatables, 2.12 meq/g; total amines, 1.81 meq/g; primary amines, 1.39 meq/g; tertiary amines, 0.43 meq/g, and water, 0.21%. It is to be noted that total amine value was high and the tertiary amine functionalities were largely intact. The total acetylatables value was only slightly elevated from that of the starting material (1.98 meq/g), and the calculated value for secondary amine (total amine-primary amine-tertiary amine) was zero within experimental error.

EXAMPLE 2

Amination of Polypropoxylate of 2,4-Diamino-2-Methylpentane Under More Severe Conditions The procedure of Example 1 was repeated with the following changes in conditions: 25.0 g of $NH_3$, 500 psig initial $H_2$ pressure, 244° C. reaction temperature, 42 minutes reaction time. Pressure decreased from 1303 to 1210 psig during this time.

Product Analysis:

| Total acetylatables | = | 2.20 meq/g |
|---|---|---|
| Total amines | = | 2.15 meq/g |
| Primary amines | = | 1.59 meq/g |
| Tertiary amines | = | 0.28 meq/g |
| Water | = | 0.14% |

It can be noted that the total amination and primary amines values were somewhat higher than in Example 1, but that the total acetylatables and secondary amines values also were higher at the expense of tertiary amines.

EXAMPLE 3

Amination of Higher Molecular Weight, 2,4-Diamino-2-Methylpentane Polypropoxylate The procedure of Example 1 was repeated except the starting material had a molecular weight of 3101 (anal.: total acetylatables=1.29 meq/g, % water=0.07 wt %). Other significant changes were as follows: 16.0 g $NH_3$, 397 initial $H_2$ psig, 235° C. operating temperature. Product analysis:

EXAMPLE 4

| Total acetylatables | = | 1.50 meq/g |
|---|---|---|
| Total amines | = | 1.38 meq/g |
| Primary amines | = | 0.94 meq/g |
| Tertiary amines | = | 0.33 meq/g |
| Water | = | 0.10% |

Amination of High Molecular Weight Polypropoxylated 2,4-Diamino-2-Methylpentane with Ni/Cu/Cr Catalyst The procedure of Example 3 was followed 3 was followed, with the following significant deviations. Catalyst was 30.0 g of the Ni/Cu/Cr catalyst of U.S. Pat. No. 3,654,370 to Yeakey with 21.0 g $NH_3$, 234° C. operating temperature, 25 minutes reaction time.

Product Analysis:

| Total acetylatables | = | 1.48 meq/g |
|---|---|---|
| Total amines | = | 1.53 meq/g |
| Primary amines | = | 1.19 meq/g |
| Tertiary amines | = | 0.40 meq/g |
| Water | = | 0.09% |

The product had an even higher amine content and in particular, a higher tertiary amine content than the product of Example 3.

EXAMPLE 5

Amination of High Molecular Weight Polypropoxylated 2,4-Diamino-2-Methylpentane at More Severe Conditions The procedure of Example 4 was repeated with the following changes: 31.525 g of Ni/Cu/Cr catalyst, 19.4 g $NH_3$, 127.11 g of 3101 molecular weight polypropoxylated diamine, 242° C. operating temperature, 35 minute reaction time.

Product analysis:

| Total acetylatables | = | 1.57 meq/g |
|---|---|---|
| Total amines | = | 1.70 meq/g |
| Primary amines | = | 1.04 meq/g |
| Tertiary amines | = | 0.25 meq/g |
| Water | = | 0.12% |

As in the use of Raney 3000, Ni/Cu/Cr at more severe conditions caused a higher total conversion, but slightly lower selectivity to the tertiary amine.

EXAMPLES 6, 7, and 8

Amination of Polypropoxylated t-Butylamine and i-Propylamine

The procedure of Example 1 was used according to conditions listed in Table I, except the starting materials were polypropoxylated isopropylamine (approximately 9 moles propylene oxide) or polypropoxylated tertiary butylamine (analysis: Total acetylatables=3.725 meq/g; total amines=1.84 meq/g; tertiary amines=1.81 meq/g; primary amines=0.01 meq/g). Results are shown in Table I.

TABLE I

| Example No. | N—alkyl Group | Grams of Raney 3000 | Grams of NH₃ | Initial Psig |
|---|---|---|---|---|
| 6 | Isopropyl | 16.03 | 25.0 | 426 |
| 7 | tert-butyl | 18.00 | 26.1 | 392 |
| 8 | tert-butyl | 22.01 | 28.0 | 375 |

| | | | Product Analysis, meq/g | | | |
|---|---|---|---|---|---|---|
| Example No. | Max. psig | Avg. °C. | Time Hrs. | Tot. Acetyl. | Tot. Amines | 1° Amine | 3° Amine |
| 6 | 1234 | 242 | 0.42 | 4.96 | 4.91 | 2.51 | 1.39 |
| 7 | 1134 | 245 | 0.42 | 4.16 | 4.16 | 2.12 | 1.53 |
| 8 | 1126 | 244 | 0.50 | 4.26 | 4.43 | 2.27 | 1.67 |

EXAMPLE 9

Comparative

Amination of Polypropoxylated Triethanolamine

A one liter stirred autoclave was charged with 15.08 g of anhydrous Raney 3000 and 139.03 g of polypropoxylated triethanolamine having the following analysis:

| Total acetylatables | = | 0.549 meq/g |
|---|---|---|
| Total amines | = | 0.16 meq/g |
| Primary amines | = | 0.15 meq/g |

The procedure of Examples 1 was followed with 16.2 g NH₃, 352 psig initial pressure, 234° C. operating temperature, and 20 minute reaction time. Analysis of the product indicated the following:

| Total acetylatables | = | 0.738 meq/g |
|---|---|---|
| Total amines | = | 0.62 meq/g |
| Primary amines | = | 0.47 meq/g |
| Tertiary amines | = | 0.04 meq/g |
| Water | = | 0.13% |

This example shows that with a polypropoxylated unhindered amine, the tertiary amine functionality is severely degraded. In this case, only 27% of the original tertiary amine functionality was retained.

EXAMPLE 10

Alkoxylation Procedure a. Preparation of four mole propylene oxide adduct of 2,4-diamino-2-methylpentane To a one liter stirred autoclave was added 190 g of 2,4-diamino-2-methylpentane (1.64 moles). The autoclave was closed, flushed twice with nitrogen and then heated to 110° C. Propylene oxide (427 g, 7.6 moles) was added over a four hour period while maintaining the temperature at 120° C. Unreacted propylene oxide was collected (53 g) by heating the reaction mixture at 10mm pressure and 60° C. The product was barely pourable at ambient temperature and was almost colorless. It weighed 374 g which indicated about 3.9 moles of propylene oxide added to the amine. The hydroxyl number was 631 (645 theoretical for 4 PO adduct.

b. Preparation of a 32 mole propylene oxide adduct of 2,4-diamino-2-methylpentane To a one liter stirred autoclave was added 200 g of the product described above (4 moles PO adduct) and 4 g of 45% aqueous potassium hydroxide. About 500 ml of propylene oxide was added at a temperature of 110° C. The finished product had a molecular weight of about 820. This product was used to make a 32 mole propylene oxide adduct of 2,4-diamino-2-methylpentane. The 32 mole adduct was used in Example 1. Before the reductive amination steps, the alkaline product was neutralized, stripped of water and lights and then filtered to remove salts.

The products of this invention are represented by the formulas:

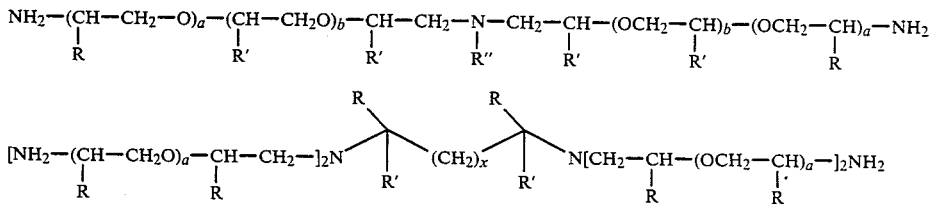

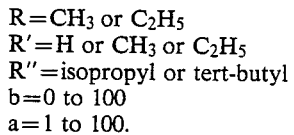

R=CH₃ or C₂H₅
R'=H or CH₃ or C₂H₅
R"=isopropyl or tert-butyl
b=0 to 100
a=1 to 100.

These polyamines are especially useful in the preparation of epoxy thermoset resins, of polyureas, and of polyamides. They are uniquely suitable in reactions with polyisocyanates to manufacture articles by reaction injection molding. Polyamides can be prepared by allowing the compounds of this invention to react with dibasic acids, diesters and diacid chlorides.

While particular embodiments of the invention have been described, it is well understood that the invention is not limited thereto since modifications may be made. It is therefore contemplated to cover by the appended claims any such modifications as fall within the spirit and scope of the claims.

What is claimed is:

1. A method for producing a bis(diaminopolyalkoxy)-N-alkylamine which comprises:
    a. alkoxylating an alkylamine to a bis(polyalkoxy)-N-alkyl amine, wherein the alkyl is a sterically hindering alkyl,
    b. catalytically aminating with ammonia to a bis(-diaminopolyalkoxy)-N-alkylamine.

2. The method of claim 1 wherein the sterically hindering alkyl is a branched alkyl of 3 to 12 carbon atoms.

3. The method of claim 1 wherein the sterically hindering alkyl is a branched alkyl of 3 to 8 carbon atoms.

4. The method of claim 1 wherein the sterically hindering alkyl is selected from the group consisting of isopropyl; tertiary butyl; iso-butyl; diisobutyl; iso-pentyl; tertiary pentyl and 1,1,3,3-tetramethylbutyl.

5. The method of claim 1 wherein the sterically hindering alkyl is selected from the group consisting of isopropyl, tertiary butyl, isobutyl and iso-pentyl.

* * * * *